United States Patent
Landau

(10) Patent No.: US 12,239,756 B1
(45) Date of Patent: Mar. 4, 2025

(54) SYSTEM AND METHOD FOR PRODUCING SCENTED INSERTS FOR USE IN CONFINED CONTAINERS

(71) Applicant: ScentSational Technologies, LLC, Jenkintown, PA (US)

(72) Inventor: Steven M. Landau, Meadowbrook, PA (US)

(73) Assignee: Scentsational Technologies, LLC, Jenkintown, PA (US)

( * ) Notice: Subject to any disclaimer, the term of this patent is extended or adjusted under 35 U.S.C. 154(b) by 416 days.

(21) Appl. No.: 17/676,801

(22) Filed: Feb. 21, 2022

(51) Int. Cl.
| | |
|---|---|
| A61L 2/23 | (2006.01) |
| B65D 77/24 | (2006.01) |
| B29C 48/00 | (2019.01) |
| B29C 48/09 | (2019.01) |
| B29C 48/13 | (2019.01) |
| B29K 105/00 | (2006.01) |

(52) U.S. Cl.
CPC .............. *A61L 2/23* (2013.01); *B65D 77/24* (2013.01); *A61L 2202/21* (2013.01); *A61L 2202/23* (2013.01); *B29C 48/0022* (2019.02); *B29C 48/09* (2019.02); *B29C 48/13* (2019.02); *B29K 2105/0029* (2013.01)

(58) Field of Classification Search
None
See application file for complete search history.

(56) References Cited

U.S. PATENT DOCUMENTS

| | | |
|---|---|---|
| 5,759,241 A | 6/1998 | Klett et al. |
| 6,123,189 A | 9/2000 | Falkenberg |
| 6,571,942 B2 * | 6/2003 | Riemenschneider ........................ B65D 81/266 206/204 |
| 7,137,570 B2 | 11/2006 | Wheatley |
| 7,306,109 B2 * | 12/2007 | Landau ................. A61K 9/0095 206/139 |
| 7,780,008 B2 | 8/2010 | Portier |
| 8,460,609 B1 | 6/2013 | Wheatley et al. |
| 9,108,763 B2 * | 8/2015 | Landau .................. B65D 25/00 |
| 10,124,941 B2 | 11/2018 | Sibley |
| 10,736,815 B1 * | 8/2020 | Landau ....................... A61J 1/14 |
| 10,744,223 B2 * | 8/2020 | Griffis .................... B65D 23/12 |

(Continued)

FOREIGN PATENT DOCUMENTS

| | | | |
|---|---|---|---|
| JP | 2000336005 A | * | 12/2000 |
| WO | WO 2016/150854 | | 9/2016 |

OTHER PUBLICATIONS

Machine translation of JP 2000-336005, retrieved from EPO database Aug. 6, 2024 (Year: 2024).*

*Primary Examiner* — Timothy Kennedy
(74) *Attorney, Agent, or Firm* — LaHorte & Associates, PC

(57) ABSTRACT

A scented insert and its method of production. A scented material is provided that is a mixture of a plastic polymer and scented oil. The scented material is melted and extruded through a die to produce a scented tubular extrusion. The extrusion die can provide contours on the exterior surface and interior surface of the scented tubular extrusion. This increases the exposed surface area and the amount of scent that can be released. The scented tubular extrusion is cut into segments. The length of the segments depends upon the scenting needs of a particular product and/or container size. The segments are inserted into the containers along with the consumables.

7 Claims, 6 Drawing Sheets

(56) References Cited

U.S. PATENT DOCUMENTS

| | | | |
|---|---|---|---|
| 11,389,557 B2 * | 7/2022 | Griffis | B65D 41/0492 |
| 2003/0000177 A1 | 1/2003 | Landau | |
| 2003/0170291 A1 * | 9/2003 | Landau | A61K 9/0095 |
| | | | 604/19 |
| 2004/0028779 A1 | 2/2004 | Landau | |
| 2004/0222108 A1 | 11/2004 | Tommarello | |
| 2005/0169813 A1 * | 8/2005 | D'Amico | A61L 9/042 |
| | | | 422/124 |
| 2006/0099168 A1 | 5/2006 | Corzani et al. | |
| 2008/0295457 A1 | 12/2008 | Kaniecki et al. | |
| 2010/0230344 A1 * | 9/2010 | Srinivas | C08J 7/02 |
| | | | 427/314 |
| 2011/0155606 A1 | 6/2011 | McKillip et al. | |
| 2015/0096266 A1 * | 4/2015 | Divine | G05B 19/4099 |
| | | | 53/558 |
| 2019/0224359 A1 * | 7/2019 | Griffis | B65D 1/0246 |
| 2021/0077648 A1 * | 3/2021 | Griffis | B65D 41/04 |

\* cited by examiner

SYSTEM AND METHOD FOR PRODUCING SCENTED INSERTS FOR USE IN CONFINED CONTAINERS

BACKGROUND OF THE INVENTION

1. Field of the Invention

In general, the present invention relates to systems and methods that are used to produce scented inserts, wherein the scented inserts are used to enhance and/or mask the natural scent of a product packaged in a container. More particularly, the present invention relates to manufacturing techniques used to fabricate the scented inserts.

2. Prior Art Description

Medications, vitamins, dietary supplements, and other consumables are typically sold in the form of tablets, pills, gummies or capsules. Forming the consumable in this manner controls intake volume and to make the product easy to consume. The various consumables are packaged in containers for sale to consumers. The containers are sealable to prevent access by children, prevent contamination, and prevent the consumables from reacting with air.

Many medications, vitamins and/or dietary supplements have strong natural odors which can get worse as the product oxidizes and ages. Often consumers find these scents to be unpleasant. The scent from the pills or capsules collects within the container and is released each time the container is opened. This causes compliance and use issues, which impacts sales and potentially health. Many manufacturers therefore prefer that a customer have a pleasant aroma experience each time their product is used. As a consequence, some manufacturers package malodorous pills and capsules with scented inserts that emit a pleasant aroma into the headspace of the container.

Scented materials are added to pill and capsule containers in different ways. Many pill and capsule containers contain desiccant packets or desiccant containers that are used to absorb moisture and, in some cases, malodors within the container. Attempts have been made to add scent to containers by adding scented material to the desiccant packets and/or desiccant canisters. However, due to the absorptive nature of desiccant materials, much of the desired scent is absorbed by the desiccant material rather than emitted by the desiccant material. Scented desiccant materials are exemplified by U.S. Pat. No. 5,759,241 to Klett.

There are scented inserts that are made of scented plastic and are not desiccants. WIPO Publication WO 2016150854, scent is added to a plastic rod. The rod can be placed inside a package, wherein the scent escapes the rod and adds scent to the surrounding environment. Other similar products exist where plastic canisters, made with scented plastic, are used to hold desiccants. There are multiple problems with such scented inserts. One problem is the low amount of active scent that can be added to a rod or canister and still have it function properly, i.e. canisters snapping together. Another issue is the ratio of surface area to size. Scent is emitted from the surfaces of the scented inserts that are exposed within a container. The scented insert must be kept small enough so it can fit inside a container and does not occupy too much of the area within a container. However, the scented insert must have a large enough surface area to emit enough scent to be effective. The result is often a compromise, wherein a scented insert is smaller than is optimal for scent release but is a good fit for the container. As a result, residual malodorous scents are not fully masked when the container is opened. The problem is exacerbated if a particular container also requires the use of a desiccant. The desiccant also occupies space within a container. In this instance, an even smaller scented insert must be used so that both the scented insert and the desiccant can fit within a full container.

Another problem associated with scented inserts is that people may mistake them for something that is edible. To prevent such situations from occurring, desiccants must have a visible consumer facing statement such as DO NOT EAT printed on its surface, and the same will be the case with scented inserts.

Another problem associated with scented inserts is that containers come in a large variety of sizes. For a variety of cost and production reasons, manufacturers prefer to add a single scented insert to a container. As such, manufacturers often buy various sized scented inserts to accommodate containers of various sizes. In some cases, such as the modified desiccant canister, the scented canister will eventually run out of enough active scent to adequately enhance the product as intended. Many manufacturers insert desiccants and scented inserts by hand. However, due to the popularity of desiccant canisters, many manufactures have invested in specialized filling equipment to automatically drop canister style, desiccants into bottles. Therefore, the ability for a similarly shaped, but differently constructed scented component that can deliver the desired scent and also be inserted using existing filling equipment would be desirable.

A need therefore exists for an improved scented insert and an improved method of making and using scented inserts that minimizes the traditional disadvantages, while also maximizing the advantages of existing size and shape of canisters on the market. This need is met by the present invention as described and claimed below.

SUMMARY OF THE INVENTION

The present invention is a scented insert and its method of production. The scented insert is added to a container in order to mask or enhance the natural aroma of consumables packaged in the container. The scented insert is extruded from a scented material. The scented material is a mixture of a plastic polymer and at least one scented oil. The scented material preferably has a melting point under 125 degrees Celsius. This enables the scented material to be melted without degrading the scent contained within the scented oil.

The scented material is melted and extruded through a die using an extrusion molding machine. The extrusion die produces a scented tubular extrusion. While manufacturing in a tubular shape can be more challenging in some ways, the benefit of added surface area and additional scent release makes the effort worthwhile. The extrusion die can produce a smooth tube or can produce an extrusion with ridges and/or troughs on the exterior surface and interior surface of the scented tubular extrusion. The ridges and troughs, if provided, increase the exposed surface area and the amount of scent that can be released by a segment of the scented tubular extrusion.

The scented tubular extrusion is cut into segments. The length of the segments depends upon the scenting needs of a particular product and/or container size. The segments are inserted into the containers with the consumables. The scented inserts are sealed within the containers and scent the head space within the container.

The tube design offers three primary benefits, the hole through the center gives the part more surface area to release scent. It has been learned through practice that when plastic is scented, some of the scent is driven bidirectionally. That is, some of the scent will travel outwards to the opposing surface. It has also been learned during manufacturing trials that making a solid part made with scent/flavor ingredients resulted in problems in properly forming the part. This resulted in deformed parts that did not cool properly. By having a hole in the center of the part, it enables the part to cool faster and keep its form. Additionally, in the case of a tube design, it was determined that scent will drive to the outer layer of the tube and some will drive to the inner part, the hole. This results in the release of scent from both the outside and the inside of the tube. The result is a greater scent release from a part, as comparted to the same shaped part without the interior surface area created by the hole. The second benefit is that a part with a hole though the center is much less likely to be mistaken for one of the supplements or other products in the bottle.

BRIEF DESCRIPTION OF THE DRAWINGS

For a better understanding of the present invention, reference is made to the following description of exemplary embodiments thereof, considered in conjunction with the accompanying drawings, in which.

DETAILED DESCRIPTION OF THE DRAWINGS

Although the present invention system and method can be embodied in many ways, only a few exemplary embodiments are illustrated. The embodiments are selected in order to set forth some of the best modes contemplated for the invention. The illustrated embodiments, however, are merely exemplary and should not be considered limitations when interpreting the scope of the appended claims.

Figure 1:
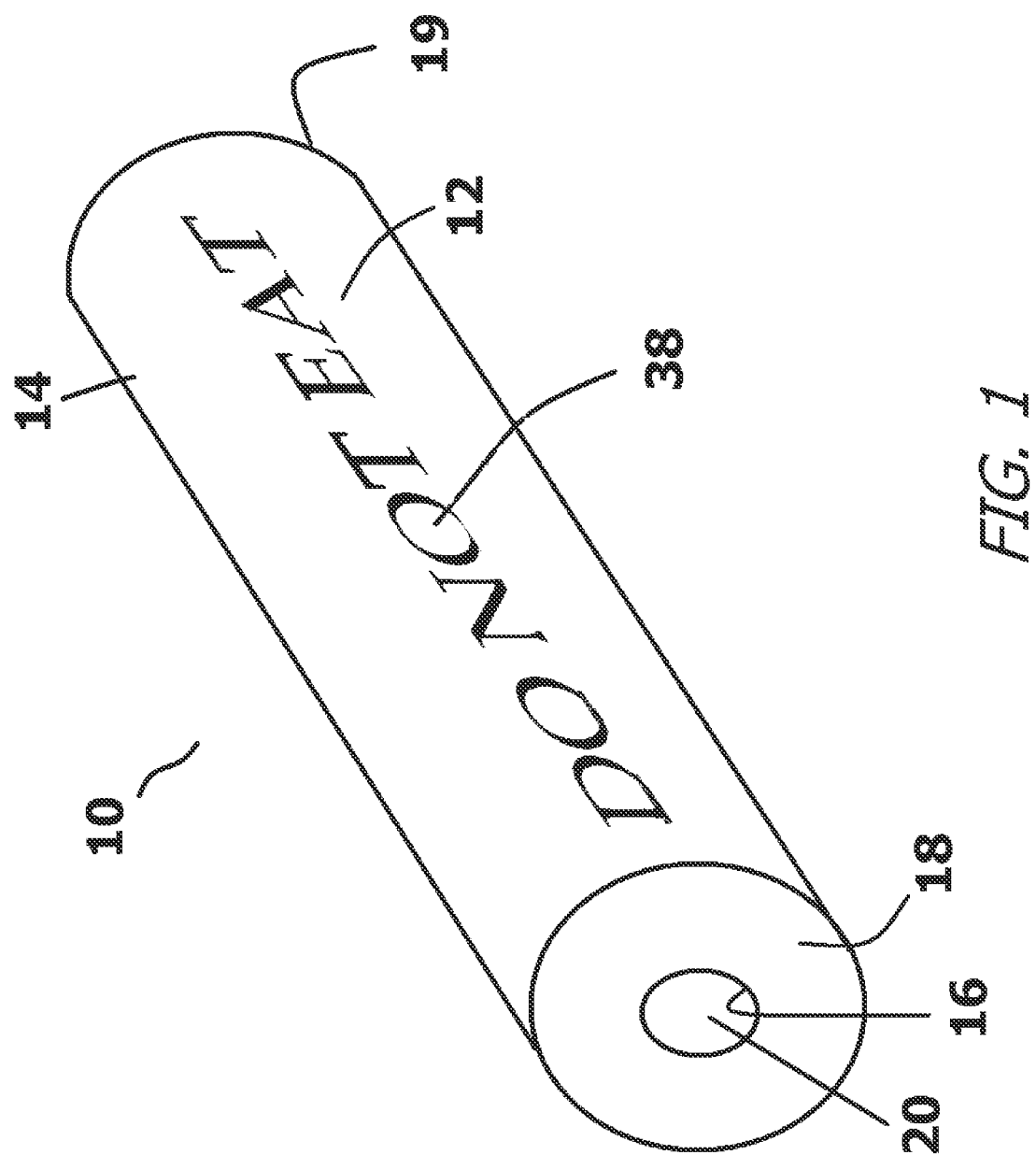
FIG. 1 is a perspective view of a first exemplary embodiment of a scented insert.

Referring to FIG. 1, a segment of a scented insert 10 is shown. The scented insert 10 is a tubular extrusion that has a peripheral wall 12 with an exterior surface 14 and an interior surface 16. Being a tubular extrusion, the scented insert 10 can have any length between a first end 18 and an opposite second end 19. The interior surface 16 of the peripheral wall 12 defines an open central conduit 20 that runs the length of the scented insert 10. In the illustrated embodiment, the exterior surface 14 is smooth in the manner of a tube or pipe. However, in other embodiments, as later shown, the exterior surface 14 of the peripheral wall 12 can be contoured. It should also be noted that in the case of a smooth walled extrusion, as is shown, the first end 18 and the second end 19 have straight cut ends that are perpendicular to the length of the central conduit 20. This differentiates the scented insert 10 from the other contents it may be packaged with.

The central conduit 20 further increases the exposed surface area of the scented insert 10 for a given length. The central conduit 20 can be smooth or have simple exterior contours, such as a heart shape or a star shape, as is later explained.

In the shown embodiment, the exterior surface 14 is smooth. Accordingly, it is able to print upon the exterior surface 14. A consumer safety statement 38, such as the words "Do Not Eat", and/or another consumer facing, or use statement can be printed or embossed onto the scented insert 10.

Figure 2:
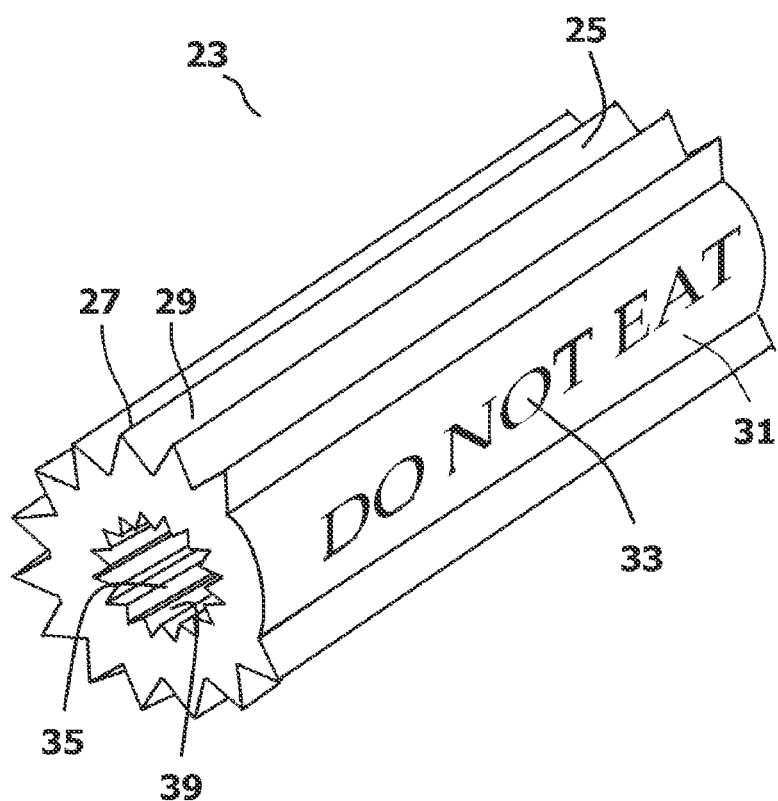
FIG. 2 is a perspective view of a second exemplary embodiment of a scented insert.
Figure 3:
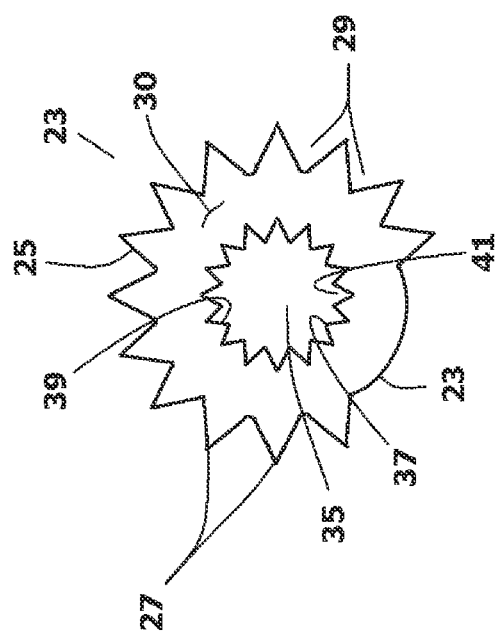
FIG. 3 is a cross-sectional view of the exemplary embodiment of FIG. 2.

Referring to FIG. 2 in conjunction with FIG. 3, an alternate embodiment of a scented insert 23 is shown. The scented insert 23 has an exterior surface 25 contains both ridges 27 and troughs 29. The ridges 27 and troughs 29 maximize the surface area along the exterior surface 25 of the scented insert 23. The ridges 27 and troughs 29 make printing more complicated. To simplify matters, a smooth area 31 can be created on the exterior surface 25 between ridges 27. The smooth area 31 is made large enough to accommodate a printed warning 33 or other identifier.

In this embodiment, the scented insert 23 has an interior surface 39 that defines a central conduit 35. The interior surface 39 further increases the exposed surface area of the scented insert 23 for a given length. The interior surface 39 can be smooth or have simple exterior contours, such as a heart shape. However, shapes, such as star-shapes, gear-shapes or the like produce complex surfaces with high ridges 37 and low troughs 39. The ridges 37 and troughs 41 maximize the surface area exposed to the central conduit 35.

Since the exterior surface 25 and the interior surface 39 of the scented insert 23 are shaped to maximize surface area, the exposed surface areas on the scented insert 23 are greater than if the scented insert 23 were merely formed as a simple cylinder. The result is a scented insert 23 that is capable of releasing more scent as compared to a cylindrical insert made of the same material.

Figure 5:
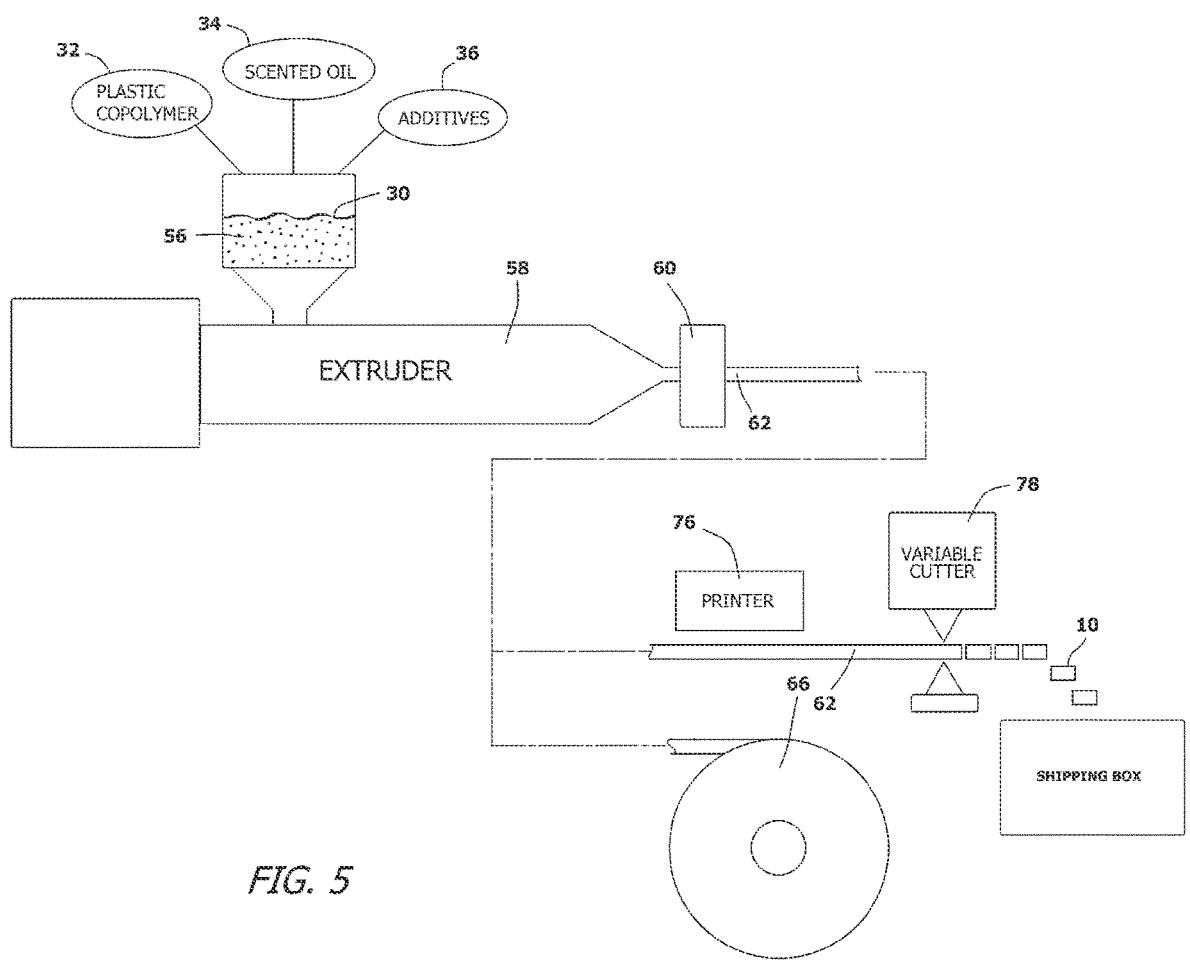
FIG. 5 is a schematic showing a first methodology used in manufacturing the present invention scented insert.

Referring to FIG. 5, it will be understood that regardless to whether the scented insert is smooth, such as in FIG. 1, or contoured, such as in FIG. 2, the scented insert is extruded from a scented material 30 that is a mixture of a plastic copolymer 32 and a scented oil 34. The scented material 30 is melted and extruded into the shape of the scented insert. The scented material 30 is preferably made from a plastic copolymer 32 with a low melting point, such as, polyolefins, polyamides, polyesters, polyethylene, ethylene-methyl acrylate, ethylene vinyl acetate, thermoplastic elastomers, ethylene n-butyl acrylate and/or other vinyl acetates. The melting point of the selected plastic copolymer 32 is preferably under 125 degrees Celsius. In this manner, the plastic copolymer 32 can be melted without burning or otherwise degrading any scented oils 34 that are mixed with the plastic copolymer 32.

The elastomeric copolymer 32 is mixed with one or more scented oils 34 to form the scented material 30. The scented oils 34 can be naturally occurring or derived. Acceptable scented oils 34 include animal oils, vegetable oils, mineral oils, as well as microcrystalline and paraffin wax. Both the elastomeric copolymer 32 and the scented oils 34 that are selected for use in the scented material 30 are FDA/EU approved for food packaging and be FDA/EU rated as GRAS (Generally Recognized As Safe) when used in food and drug applications. Accordingly, the selected plastic copolymer 32 and scented oil 34 are non-toxic if consumed.

Additives 36, such as colorants, can also be added to the scented material 30. It is preferred that the scented insert 10 be a different color than the consumables with which it is packaged. Additionally, parts will be made between 13 mm and 25 mm thick and between 15 mm and 30 mm long as to be consistent with other similar shaped desiccant canisters commonly used in the market. This makes the parts more easily recognized as a familiar insert by consumers, and also can be auto inserted with the same insertion equipment by manufacturers.

Figure 4:
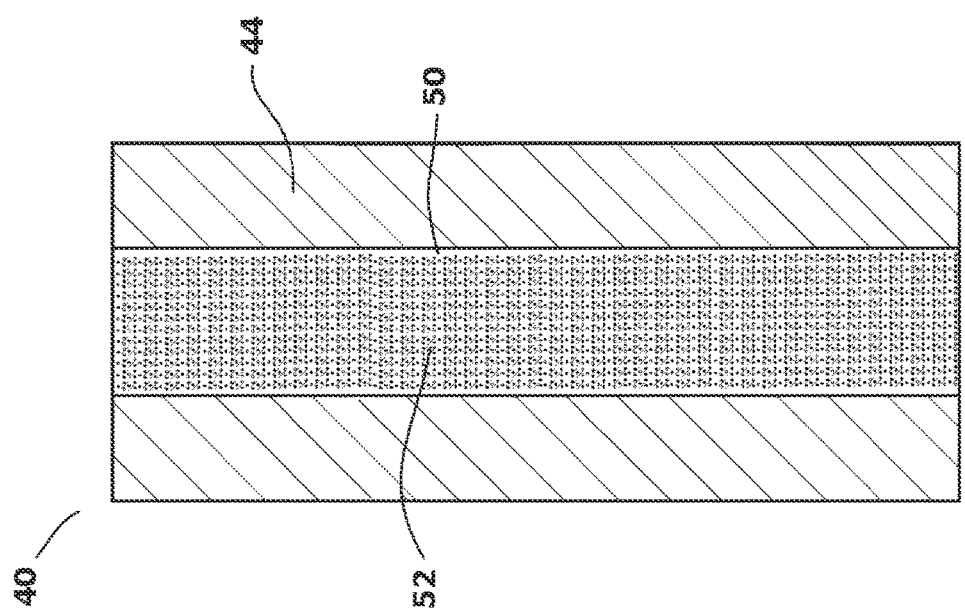
FIG. 4 is a cross-sectional view of a third exemplary embodiment of a scented insert filled with a desiccant.

Referring to FIG. 4, a modified embodiment is presented where a desiccant 52 can be used to fill the central conduit 50 of a scented insert 40. The desiccant 52 absorbs moisture. The desiccant 52 is exposed to the surrounding environment through the open ends of the central conduit 50. By placing the desiccant 52 within the scented insert 40, the use of space is maximized. Furthermore, the manufacturing process is simplified since only one item need be inserted into a container.

Referring to FIG. 5, in conjunction with FIG. 1, the first step in a manufacturing process is illustrated. The scented material 30 is a mixture of a plastic copolymer 32 and a scented oil 34. Other additives 36, such as a plasticizing oils can also be used to soften the scented material 30 and/or lower its melting point. The scented material 30 is formed into feed material 56 for an extrusion molding machine 58. The extrusion molding machine 58 heats the feed material 56 until it melts and forces the molten feed material through an extrusion die 60. The extrusion die 60 creates a continuous extrusion 62 from which the scented inserts 10 are cut. The continuous extrusion 62 is then wound onto a supply reel 66 or cut to a selected size and packaged. When sold pre-cut, the extrusion 62 passes under a printer 76 that prints warnings 38 onto the extrusion 62. The extrusion 62 is then cut to size by a cutter 78, therein producing individual scented inserts 10. The length of the scented insert 10 can be selectively controlled by adjusting the cutter 78. Accordingly, extrusion run can be used to make many different length scented inserts 10 for many different sized containers.

Figure 6:
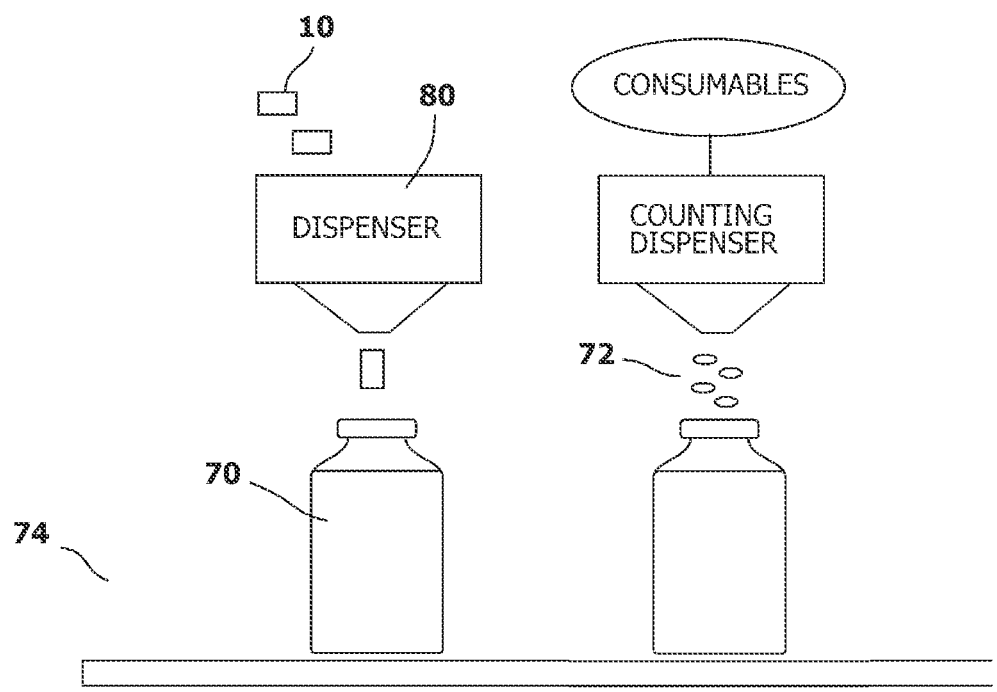
FIG. 6 is a schematic showing a packaging methodology used with the present invention scented insert.

Referring to FIG. 6, supply reels 66 that contain the continuous extrusions 62 are sold to manufacturers who fill containers 70 with consumables 72, such as gummies, supplements, powders, capsules, tablets or pills. The containers 70 are placed on an automated processing line 74 where the containers 72 are filled, sealed, labeled and packaged.

In industry, prior art desiccant canisters are made in standard sizes. There are also manufacturing equipment designed to handle the prior art desiccant canisters. Accordingly, there is benefit in making the present invention scented inserts 10 in the same size a prior art desiccant canisters. In this manner, the same handling equipment can be used in automated processing lines.

The cut scented inserts 10 are fed into a dispensing machine 80 that inserts one scented insert 10 into each of the containers 70 progressing on the automated processing line 74. The containers 70 are seal at a different station along the automated processing line 74. The result is that the consumables 72 are sealed within the container 70 with the scented insert 10. The scented insert 10 is cut to the exact length needed to both scent the container 70 and to mask or compliment the scent of the consumables 72. The scented insert 10 releases the aroma of the scented oil 34 into the container 70. The scent fills the container 70 and may even permeate the composition of the consumables 72. When the container 70 is opened, the primary scent emitted is that of the scented insert 10. Furthermore, as consumables 72 are removed from the container 70, more headspace becomes available within the container 70 that can be scented by the scented insert 10.

It will be understood that the embodiments of the present invention that are illustrated and described are merely exemplary and that a person skilled in the art can make many variations to those embodiments. All such embodiments are intended to be included within the scope of the present invention as defined by the claims.

What is claimed is:

1. A method of manufacture comprising:
   mixing a plastic polymer and at least one scented oil to produce scented material;
   melting said scented material and extruding said scented material to form a length of a scented tubular extrusion, wherein said scented tubular extrusion defines an open central conduit;
   at least partially filling said open central conduit with a material selected from a group consisting of desiccant materials and hydrating materials;
   cutting said scented tubular extrusion into segments to form scented inserts of a selected size; and
   inserting one of said segments into a container with a consumable product.

2. The method according to claim 1, wherein said scented material has a melting point under 125 degrees Celsius and is extruded at a temperature under 125 degrees Celsius.

3. The method according to claim 1, wherein extruding said scented material includes extruding said scented tubular extrusion with an exterior surface that contains ridges and troughs that run along said length of said scented tubular extrusion.

4. The method according to claim 3, wherein extruding said scented material includes extruding said scented tubular extrusion with an exterior surface that contains a section that runs along said length of said scented tubular extrusion, wherein said section is large enough to accommodate a printed message printed thereon.

5. The method according to claim 1, wherein said open central conduit extends said length of said scented tubular extrusion to maximize exposure of said scented material.

6. The method according to claim 5, wherein said scented tubular extrusion has an interior surface that faces said open central conduit, wherein said interior surface contains a contoured shape, that runs along said length of said scented tubular extrusion.

7. The method according to claim 1, further including printing a consumer facing use statement on said exterior surface of said scented tubular extrusion.

* * * * *